(12) United States Patent
McGrew et al.

(10) Patent No.: US 7,691,605 B2
(45) Date of Patent: Apr. 6, 2010

(54) SELECTION OF CELLS EXPRESSING HETEROMERIC POLYPEPTIDES

(75) Inventors: Jeffrey T. McGrew, Seattle, WA (US); Allison A. Bianchi, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 410 days.

(21) Appl. No.: 10/251,447

(22) Filed: Sep. 20, 2002

(65) Prior Publication Data

US 2003/0082735 A1    May 1, 2003

Related U.S. Application Data

(60) Provisional application No. 60/323,954, filed on Sep. 20, 2001.

(51) Int. Cl.
- C12P 21/08 (2006.01)
- C12N 5/10 (2006.01)
- C12N 5/12 (2006.01)
- C12N 15/13 (2006.01)
- C07H 21/04 (2006.01)

(52) U.S. Cl. .................. 435/69.1; 435/320.1; 435/326; 435/364; 435/365; 435/372.1; 536/23.53

(58) Field of Classification Search ................ 536/23.2, 536/23.4, 23.53; 435/320.1, 326, 252.33, 435/361.45, 372.1, 357, 358, 69.1
See application file for complete search history.

(56) References Cited

U.S. PATENT DOCUMENTS

| | | | |
|---|---|---|---|
| 5,545,503 A | 8/1996 | Yamazaki | |
| 5,624,818 A | 4/1997 | Eisenman et al. | |
| 5,840,869 A | 11/1998 | Mosley et al. | |
| 5,916,771 A | 6/1999 | Hori et al. | |
| 5,928,904 A | 7/1999 | Holmes et al. | |
| 6,129,914 A * | 10/2000 | Weiner et al. | |
| 6,270,964 B1 | 8/2001 | Michnick et al. | |
| 6,294,330 B1 | 9/2001 | Michnick et al. | |
| 6,428,951 B1 | 8/2002 | Michnick et al. | |

FOREIGN PATENT DOCUMENTS

| | | |
|---|---|---|
| WO | WO 98/13502 | 4/1998 |
| WO | WO 98/34120 | 8/1998 |
| WO | WO 98/44350 | 10/1998 |
| WO | WO 01/27299 | 4/2001 |
| WO | WO 01/38557 | 5/2001 |

OTHER PUBLICATIONS

Stryer et al, in Biochemistry, Third edition, W H Freeman Company, New York, pp. 31-33, 1998.*
Blakely et al, Nature Biotechnology 18: 218-222, Feb. 2000.*
Kim et al, Biotechnol Prog 17: 69-75, Jan.-Feb. 2001.*
Murre et al., Interactions between Heterologous Helix-Loop-Helix Proteins Generate Complexes That Bind Specifically to a Common DNA Sequence *Cell* 58:537-544 (1989).
Wood et al., High Level Synthesis of Immunoglobulins in Chinese Hamster Ovary Cells *J. I.* 145:3011-3016 (1990).
Marmonstein et al., DNA recognition by GAL4: structure of a protein-DNA complex *Nature* 356:408-414 (1992).
Kurokawa et al., Differential orientations of the DNA-binding domain and carboxy-terminal dimerizaton interface regulate binding site selection by nuclear receptor heterodimers *Genes Dev* 7:1423-1435 (1993).
Zhang et al., Antibody-promoted dimerization bypasses the regulation of DNA binding by the heme, domain of the yeast transcriptional activator HAP1 *Proc. Natl. Acad Sci USA* 90:2851-2855 (1993).
Nixon et al., Assembly of an active enzyme by the linkage of two protein modules *Proc. Natl. Acad Sci* 94:1069-1073 (1997).
Pelletier et al., Oligomerization domain-directed reassembly of active dihydrofolate reductase from rationally designed fragraments *Proc. Natl. Acad. Sci* 95:12141-12146 (1998).
Remy and Michnick , Clonal selection and in vivo quantitation of protein interactions with protein-fragment complementation assays *Proc. Natl. Acad. Sci* 96:5394-5399 (1999).
Arndt et al., A Heterodimeric Coiled-coil Peptide Pair Selected in Vivo from a Designed Library-versus-Library Ensemble *JMB* 295:627-639 (2000).
Morimoto et al., High level expression of a human rabies virus-neutralizing monoclonal antibody by a rhabdovirus-based vector *J. of Imm. Methods* 252:199-206 (2001).
Remy and Michnick, Visualization of biochemical networks in living cells *Proc. Natl. Acad. Sci* 98:7678-7683 (2001).
Mossner et al., "Fast selection of antibodies without antigen purification: adaptation of the protein fragment complementation assay to select antigen-antibody pairs" J of Molecular Biology, 308,2: 115-122 (2001).
Lucas, et al., "High-level production of recombinant proteins in CHO cells using a dicistronic DHRF intron expression vector" Nucleic Acids Research, Oxford University Press, 24, 9: 1174-1179 (1996).
Bianchi, et al., "High-level expression of full-length antibodies using trans-complementing expression vectors." Biotechnology and Bioengineering, 84, 4: 439-444 (2003).
Stryer, et al., Biochemistry, "Levels of Structure in Protein Architecture" Third Edition pp. 31-33 (1988).
Rudikoff, et al., Proc Natl Acad Sci USA, "Single amino acid substitution altering antigen-binding specificity" 79, pp. 1979-1983(1982).
Kobrin, et al., J of Immunology, "A V Region Mutation in a Phosphocholine-Binding Monoclonal Antibody Results in Loss of Antigen Binding" 146 pp. 2017-2020 (1991).
Barrios, et al., J Molecular Recognition, "Length of the antibody heavy chain complementarity determining region 3 as specificity-determining factor" 17 pp. 332-2338 (2004).

\* cited by examiner

*Primary Examiner*—Phuong Huynh
(74) *Attorney, Agent, or Firm*—Randolph N. Mohr

(57) ABSTRACT

This invention relates to the general field of recombinant expression of polypeptides in animal cell culture. More particularly, the invention concerns improved selection in cells of recombinantly engineered vectors designed to express polypeptides.

36 Claims, 1 Drawing Sheet

```
                         SEQUENCE LISTING

<160> NUMBER OF SEQ ID NOS: 9

<210> SEQ ID NO 1
<211> LENGTH: 41
<212> TYPE: DNA
<213> ORGANISM: Artificial
<220> FEATURE:
<223> OTHER INFORMATION: PCR Primer

<400> SEQUENCE: 1
atatctcgag atccgtgcca tcatgtctga ccgtatgaaa c                       41

<210> SEQ ID NO 2
<211> LENGTH: 44
<212> TYPE: DNA
<213> ORGANISM: Artificial
<220> FEATURE:
<223> OTHER INFORMATION: PCR Primer

<400> SEQUENCE: 2
gccaccgccg gatccaccgc caccccgctc gcctaccagc tttt                    44

<210> SEQ ID NO 3
<211> LENGTH: 45
<212> TYPE: DNA
<213> ORGANISM: Artificial
<220> FEATURE:
<223> OTHER INFORMATION: PCR Primer

<400> SEQUENCE: 3
ggtggatccg gcggtggcgg cggctcaatg gttcgaccat tgaac                   45

<210> SEQ ID NO 4
```

```
<211> LENGTH: 33
<212> TYPE: DNA
<213> ORGANISM: Artificial
<220> FEATURE:
<223> OTHER INFORMATION: PCR Primer

<400> SEQUENCE: 4
atatcaattg ttattccggt tgttcaataa gtc                                    33

<210> SEQ ID NO 5
<211> LENGTH: 187
<212> TYPE: PRT
<213> ORGANISM: Mus musculus

<400> SEQUENCE: 5
```

Met Val Arg Pro Leu Asn Cys Ile Val Ala Val Ser Gln Asn Met Gly
1               5                   10                  15

Ile Gly Lys Asn Gly Asp Leu Pro Trp Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

```
<210> SEQ ID NO 6
<211> LENGTH: 45
<212> TYPE: DNA
<213> ORGANISM: Artificial
<220> FEATURE:
<223> OTHER INFORMATION: PCR Primer

<400> SEQUENCE: 6
gtggatccgg cggtggcggc ggctcattgg caagtaaagt agaca               45

<210> SEQ ID NO 7
<211> LENGTH: 33
<212> TYPE: DNA
<213> ORGANISM: Artificial
<220> FEATURE:
<223> OTHER INFORMATION: PCR Primer

<400> SEQUENCE: 7
atatcaattg ttagtctttc ttctcgtaga ctt                            33
```

```
-continued

<210> SEQ ID NO 8
<211> LENGTH: 38
<212> TYPE: DNA
<213> ORGANISM: Artificial
<220> FEATURE:
<223> OTHER INFORMATION: PCR Primer

<400> SEQUENCE: 8
gataatatgg ccacaaccat gtctgaccgt atgaaaca                              38

<210> SEQ ID NO 9
<211> LENGTH: 11
<212> TYPE: PRT
<213> ORGANISM: Artificial
<220> FEATURE:
<223> OTHER INFORMATION: protein linker

<400> SEQUENCE: 9

Gly Gly Gly Gly Ser Gly Gly Gly Gly Gly Ser
1               5                   10
```

SELECTION OF CELLS EXPRESSING HETEROMERIC POLYPEPTIDES

This application claims the benefit under 35 U.S.C. section 119 to U.S. provisional application Ser. No. 60/323,394 filed Sep. 20, 2001.

FIELD OF THE INVENTION

This invention relates to the general field of recombinant expression of polypeptides in animal cell culture. More particularly, the invention concerns improved selection in cells of recombinantly engineered vectors designed to express polypeptides.

BACKGROUND OF THE INVENTION

Many commercially important proteins are produced in recombinantly engineered cells that have been adapted for long term growth in culture. Frequently, the proteins are expressed as a single polypeptide chain. Also expressed in these cells are multiple heterologous polypeptides that can associate to form heteromeric complexes, such as for example, an antibody, which is formed by the expression of equal parts of heavy chains and light chains.

One difficulty that can be encountered when expressing heteromeric complexes in cells is obtaining appropriate amounts of each of the recombinant polypeptides that form a component of the complex. For example, in the expression of an antibody frequently either the heavy chain or the light chain are expressed to relatively high levels with respect to the corresponding partner; however, obtaining a cell line expressing both chains to high levels and in roughly equal amounts is difficult.

These difficulties result in additional steps and also repetition of steps in the process of generating cell lines expressing recombinant polypeptides resulting in delays which also substantially increase costs associated with recombinant expression of the polypeptides. Thus, there is a need in the art for simpler methods of selecting for high level expression of polypeptides in cell cultures so as to increase production of the polypeptides thereby reducing the cost and time investment necessary for selection of cells expressing the polypeptides. The invention fulfills this need by providing an improved method for selecting cells expressing polypeptides.

SUMMARY OF THE INVENTION

The invention is based, in part, on the premise that the efficient production of recombinant heteromeric complexes in cells is improved if each component of the complex is expressed in proportional amounts. As such, the present invention provides methods and compositions to select for recombinantly engineered cells that express more than one polypeptide, where the polypeptides are expressed in proportional quantities such that the polypeptides can efficiently associate to form a heteromeric complex and higher expression is achieved.

In one embodiment, the invention comprises two vectors, where each vector comprises at least two open reading frames encoding two different polypeptides. In this embodiment, a first vector encodes a first polypeptide that can associate with a corresponding first polypeptide encoded by the second vector to form a heteromeric complex. In addition, the first vector encodes a second polypeptide that can associate with a corresponding second polypeptide encoded by the second vector to form a heteromeric complex having a selectable activity.

In a particular embodiment, the invention contemplates an isolated nucleic acid molecule comprising a first nucleic acid encoding a polypeptide, wherein said first nucleic acid is operably linked to a second nucleic acid encoding a subunit of a selectable marker, and wherein said subunit or subunits is capable of interacting with a different subunit of the selectable marker thereby providing a selectable activity.

In another embodiment the invention contemplates an isolated nucleic acid molecule comprising a first nucleic acid encoding a polypeptide, wherein said first nucleic acid is operably linked to a second nucleic acid encoding a subunit of a selectable marker, and wherein said subunit or subunits is capable of interacting with a different subunit of the selectable marker thereby providing a selectable activity, and further comprising a third nucleic acid encoding a polypeptide that is capable of associating with the polypeptide encoded by the first nucleic acid to form a heteromeric complex, wherein said third nucleic acid is operably linked to a fourth nucleic acid encoding at least one subunit of a selectable marker, and wherein said subunit or subunits are capable of associating with the polypeptide selectable marker subunit encoded by the second nucleic acid, thereby providing a selectable activity.

In another particular embodiment, the heteromeric complex described above is an antibody, and the selectable marker described above is selected from the group consisting of a drug resistance marker, a metabolic survival marker, a color marker and a fluorescent marker.

The invention further provides methods for constructing the nucleic acid molecules of the invention, methods for making host cells expressing nucleic acids of the invention, host cell lines expressing the nucleic acids of the invention, and methods for producing and isolating heteromeric complexes recombinantly expressed from the nucleic acids in host cells.

DETAILED DESCRIPTION OF THE INVENTION

Figure 1:
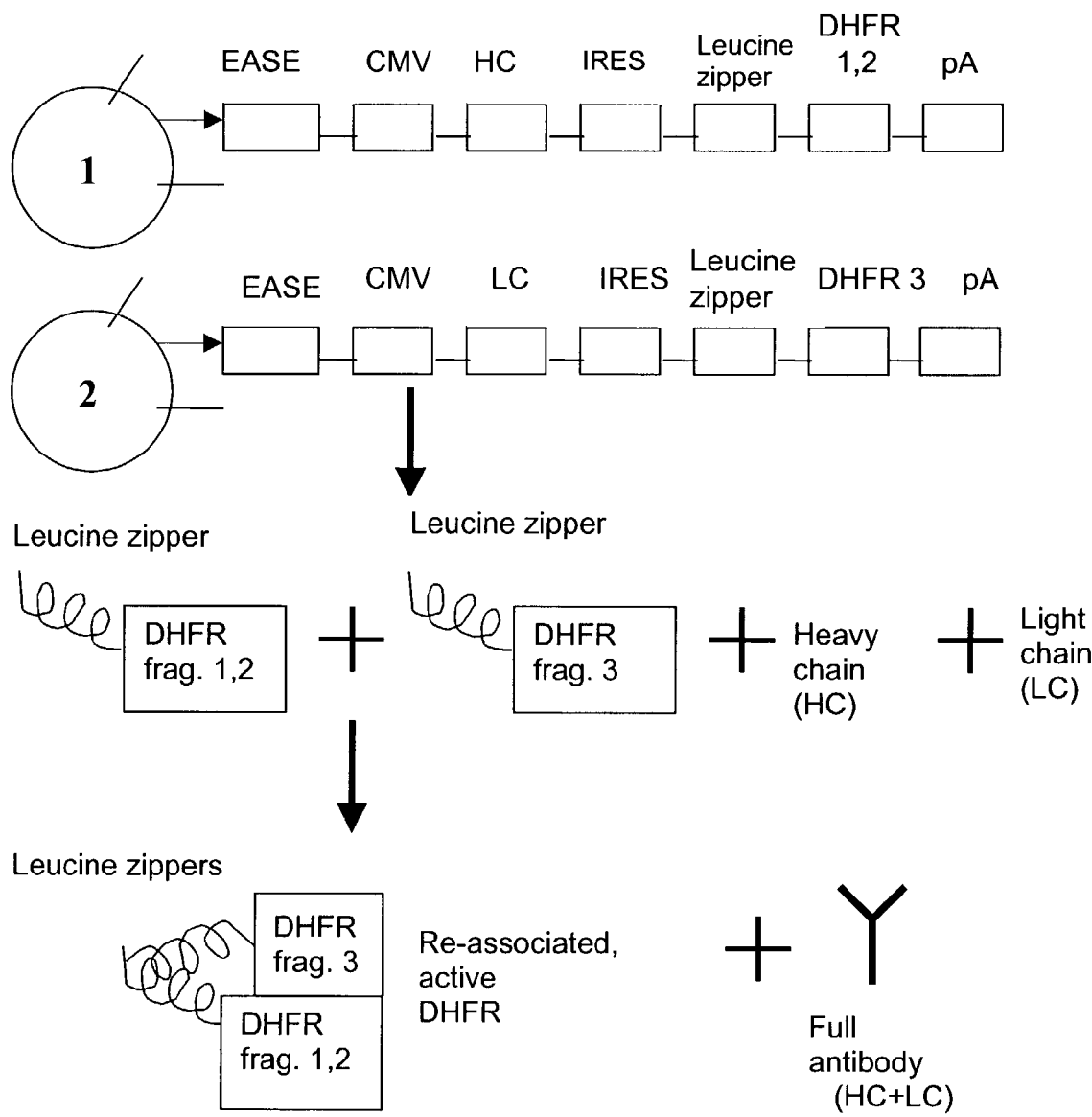
FIG. 1. A schematic representation of the nucleic acid constructs utilized in the examples, each comprising a subunit of a selectable marker and expressing different polypeptides, which can associate to form a heteromeric complex in a cell. The abbreviations are as follows: EASE, expression augmenting sequence element; CMV, cytomegalovirus promoter; HC, Heavy Chain; LC, Light Chain; IRES, internal ribosomal entry site; DHFR, dihydrofolate reductase; and pA, polyadenylation signal.

Efficient production of recombinant heteromeric complexes in cells is improved if each component of the complex is expressed in proportional and high amounts. The present invention provides methods and compositions to select for recombinantly engineered cells, which express more than one heterologous polypeptide in proportional quantities such that the polypeptides can efficiently associate to form a heteromeric complex at higher expression levels than traditionally prepared heteromeric complexes. The present invention is also advantageous in that it decreases the time required to select for cells expressing high levels of a desired recombinant heteromeric polypeptide complex.

The invention utilizes selectable markers that can exist as two or more subunits that when expressed together will interact, thereby providing a selectable activity. The individual subunits do not have significant selectable activity alone, but do provide selectable activity when co-expressed with their counterpart subunit. The optimal activity of the subunits can depend upon their interaction, and as such can be facilitated by interaction domains. Such interaction domains can be endogenous to the subunit or it can be heterologous to the subunit.

Nucleic acid molecules are constructed that encode a polypeptide and a subunit of the selectable marker, arranged in such a way that expression of the subunit correlates with expression of the polypeptide. Thus, when the nucleic acid molecules encoding both subunits are transfected into cells and selective conditions applied, approximately equal and high levels of expression of each of the subunits will provide the highest selectable activity. In addition, the operably linked polypeptides will be expressed in nearly equal and high amounts, therefore there is optimization of selection of cells expressing equal and high levels of the desired polypeptides.

In one non-limiting embodiment, the invention entails the use of two subunits of a selectable marker, each expressed as a fusion protein to an interaction domain. When expressed, the interaction domain promotes association or dimerization of the two subunits thereby allowing the subunits to function and providing a selectable activity (e.g., but not limited to, that described by Pelletier et al. (1998), Proc. Natl. Acad. Sci., 95:12141-12146).

In an alternative embodiment, the invention entails the use of three subunits of a selectable marker, each expressed as a fusion protein to an interaction domain, thereby enhancing association to provide a selectable activity. In this embodiment, there are three components of the heteromeric complex. In the expressed vector(s) coding sequences for each are operably linked to coding sequences for each of the respective subunits of the selectable marker, for example, a bispecific antibody expressing a single heavy chain and two different light chains, wherein the two light chains are both capable of associating with the heavy chain. The invention also encompasses use of selectable markers known or yet to be disclosed that have four or even more subunits.

As will be shown below in the examples, it has been discovered that the methods and compositions of the invention reduce the amount of time necessary to select for the desired cells expressing high levels of a single polypeptide. Thus, in yet another embodiment, the invention encompasses selecting for cells expressing high levels of a recombinant polypeptides.

In some embodiments, the nucleic acids encoding the selectable marker subunits are fused in frame to a nucleic acid encoding a linker, which is then fused in frame to a nucleic acid encoding an interaction domain. Linkers can include any relatively short, flexible sequence that allows the interaction domain to interact and for the subunits to function to provide a selectable activity. Examples of linkers are abundant in the relevant art and can comprise GGPGG, GPGGG, where in single letter amino acid codes, G is glycine and P is proline. In one embodiment, the linker is GGGGSGGGGS SEQ ID NO: 9 (Curtis et al. (1991), Proc Natl Acad Sci 88(13):5809-5813).

An interaction domain is a domain, including but not limited to, polypeptides capable of facilitating the interaction or association of two or more homologous or heterologous polypeptides. As used herein, the terms "associating" or "interacting" are meant to describe a relationship between at least two molecules wherein one molecule binds to the others and/or affects the activity of the others. Interaction can include the direct or indirect binding of two polypeptides (or polypeptide and nucleic acid), or the functional activation or inhibition of a molecule's activity by another molecule.

In one embodiment, the interaction domain is a dimerization domain. A dimerization domain can be a polypeptide capable of inducing interaction or association of two polypeptides. There are two types of dimers, those capable of forming homodimers (with the same sequence), or heterodimers (with another sequence).

In one illustrative but non-limiting embodiment, the interaction domain is a leucine zipper coiled coil polypeptide. A leucine zipper typically comprises about 35 amino acids containing a characteristic seven residue repeat with hydrophobic residues at the first and fourth residues of the repeat (Harbury et al. (1993), Science 262:1401). Thus a leucine zipper is amenable to fusion to a polypeptide for the purpose of oligomerizing the polypeptide as it is a small molecule and is less likely to disrupt the polypeptides normal function than would a larger interaction domain. Examples of leucine zippers include but are not limited leucine zipper domains from polypeptides such as GCN4, C/EBP, c-Fos, c-Jun, c-Myc and c-Max.

Additional examples of dimerization domains include helix-loop-helix domains (Murre et al. (1989), Cell 58:537-544). The retinoic acid receptor, thyroid hormone receptor, other nuclear hormone receptors (Kurokawa et al. (1993), Genes Dev. 7:1423-1435) and yeast transcription factors GAL4 and HAP1 (Marmonstein et al. (1992), Nature 356:408-414; Zhang et al. (1993), Proc. Natl. Acad. Sci. USA 90:2851-2855; U.S. Pat. No. 5,624,818) all have dimerization domains with this motif.

In yet another embodiment, the interaction domain is a tetramerization domain, which is a polypeptide capable of binding three other tetramerization domains to form a tetrameric complex. Examples of proteins containing tetramerization domains include but are not limited to the *E. coli* lactose repressor (amino acids 46-360; Chakerian et al. (1991), J. Biol. Chem. 266:1371; Alberti et al. (1993), EMBO J. 12:3227; and Lewis et al. (1996), Nature 271:1247), and the p53 tetramerization domain at residues 322-355 (Clore et al. (1994), Science 265:386; Harbury et al. (1993), Science 262:1401; U.S. Pat. No. 5,573,925).

In one embodiment, the two subunits are expressed from two vectors, wherein the first vector comprises a first nucleic acid encoding a first polypeptide, and wherein the first nucleic acid is operably linked to a second nucleic acid encoding a subunit of a selectable marker. The second vector comprises a third nucleic acid encoding a polypeptide that is capable of associating with the polypeptide encoded by the first nucleic acid, wherein the third nucleic acid is operably linked to a fourth nucleic acid encoding a different subunit of the selectable marker. Thus, both vectors are simultaneously transfected into a cell population and selection for expression of the selectable marker (comprised of two subunits) is applied.

In another embodiment, the invention further comprises a nucleic acid encoding a different functional selectable marker, in addition to a subunit of a selectable marker and a polypeptide of a heteromeric complex. For purposes herein, a "different functional selectable marker" is not a subunit of a selectable marker, but is a protein with fully functional selectable activity. Well known markers such as zeomycin, neomycin, puromycin, Blasticidin S, or GPT which confers resistance to mycophenolic acid, etc., can be used as different functional selectable markers. In this embodiment, the invention comprises two vectors, wherein each of the vectors comprises a first nucleic acid encoding a polypeptide that can form a heteromeric complex operably linked to a second nucleic acid encoding at least one subunit of a selectable marker, as well as also a nucleic acid encoding a different, functional selectable marker. Further, the respective polypeptides encoded by the first nucleic acid of each vector can associate to form a complex, and the subunit or subunits encoded by the second nucleic acid of each vector can associate to provide a selectable activity and the polypeptides encoded by the third nucleic acids provide selectable activities different than the selectable activity of the subunits encoded by the second nucleic acids. For example, the first vector can encode resistance to neomycin and the second vector can encode resistance to zeomycin or only one vector can contain the additional different functional selectable marker. Thus, one vector is transfected into a cell line and selection is applied (i.e., the drug G418 is added to neomycin resistant cells). After selection, conventional methods can be used to determine the presence of the vector and the expression level of the polypeptides encoded by the nucleic acids on the vector, for example by PCR, Southern blot, ELISA, western blot, and the like. Once high level expression has been obtained, the second vector is transfected into the cell line. While maintaining selection for the first vector, selection is applied for the second selectable marker (i.e., zeomycin resistance) and the presence of the second vector and expression of the respective vector encoded proteins are assessed. In this embodiment, once it has been determined that both vectors are present, selection is applied for expression of the subunits that have associated in the cell to provide a selectable activity, e.g., dihydrofolate reductase (DHFR), as described above.

In an alternative embodiment, both the nucleic acids of the invention encoding independent selectable activities are transfected simultaneously and selection is applied at the same time. Once it has been determined that both vectors are present, selection is applied for expression of the subunits that have associated in the cell to provide a selectable activity, e.g., dihydrofolate reductase (DHFR), as described above.

In yet another embodiment, the vectors of the invention encoding independent selectable activities are each transfected into separate cell lines. Once selection is applied and clones have been identified that express high levels of the proteins encoded by each desired vector, the cells are fused as described in Hori et al. (U.S. Pat. No. 5,916,771). Once fusion is complete, selection is applied for the selectable activity provided by the subunits.

In yet another embodiment, nucleic acids of the invention optionally not containing an independent selectable activity are transfected simultaneously with a third vector. The third vector encodes for a separate selectable activity, such as for example, neomycin resistance or beta galactosidase that can allow for a preliminary selection of cells that were successfully transfected. Once this preliminary selection has been performed, selection can be applied for the selectable activity of the subunits, e.g., DHFR. In this embodiment, equal quantities of the two expression vectors are transfected while the third vector is transfected at one-third the concentration of the first two vectors (e.g., a ratio of 3:3:1 or 6:6:1 or the like). One of skill in the art will recognize that variations in the ratios are within the scope of the invention.

The nucleic acids encoding a component of the desired heteromeric complex can be obtained as a cDNA or as a genomic DNA by methods known in the art. For example, messenger RNA coding for a desired component can be isolated from a suitable source employing standard techniques of RNA isolation, and the use of oligo-dT cellulose chromatography to segregate the poly-A mRNA. When the heteromeric complex to be expressed is an antibody, suitable sources of desired nucleic acids can be isolated from mature B cells or a hybridoma culture. In addition, the nucleic acids for use in the invention can be obtained by chemical synthesis.

The term "heteromeric complex" is meant to include a molecular complex formed by the association of at least two different molecules. The association can be non-covalent interaction or covalent attachment, e.g., disulfide bonds. The two different molecules are typically two different polypeptides, however, the invention contemplates heteromeric complexes between polypeptides and nucleic acids and between different nucleic acids. In one embodiment, the heteromeric complex provides a functional activity, such as, the ability to bind a substrate (e.g., an immunoglobulin capable of binding a corresponding antigen), enzymatic activity or the like. In one embodiment, the heteromeric complex of the invention is secreted into the culture medium of the host cell in which it is being produced.

In a particular embodiment, the heteromeric complex is an immunoglobulin molecule. The immunoglobulin in vertebrate systems is an antibody comprised of two identical light chains and two identical heavy chains. The four chains are joined together by disulfide bonds, such that each light chain is joined with a heavy chain and the heavy chains are connected across their tails altogether forming a Y-shaped heteromeric complex. Numerous techniques are known by which DNA encoding immunoglobulin molecules can be manipulated to yield DNAs capable of encoding recombinant proteins such as antibodies with enhanced affinity, or other antibody-based polypeptides (see, for example, Larrick et al. (1989), Biotechnology 7:934-938; Reichmann et al. (1988), Nature 332:323-327; Roberts et al. (1987), Nature 328:731-734; Verhoeyen et al. (1988), Science 239:1534-1536; Chaudhary et al. (1989), Nature 339:394-397).

Recombinant cells producing fully human antibodies (such as are prepared using antibody libraries, and/or transgenic animals, and optionally further modified in vitro), as well as humanized antibodies can also be used in the invention. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger et al., WO 86/01533; Neuberger et al., European Patent No. 0,194,276 B1; Winter, U.S. Pat. No. 5,225,539; Winter, European Patent No. 0,239,400 B1; Queen et al., European Patent No. 0,451,216 B1; and Padlan et al., European Patent No. 0,519,596 A1. For example, the invention can be used to induce the expression of human and/or humanized antibodies that immunospecifically recognize specific cellular targets, e.g., the human EGF receptor, the her-2/neu antigen, the CEA antigen, Prostate Specific Membrane Antigen (PSMA), CD5, CD11a, CD18, NGF, CD20, CD45, Ep-cam, other cancer cell surface molecules, TNF-alpha, TGF-b 1, VEGF, other cytokines, alpha 4 beta 7 integrin, IgEs, viral proteins (for example, cytomegalovirus), etc., to name just a few.

Examples of heteromeric complexes, in addition to immunoglobulins, include but are not limited to any heterodimeric or hetero-oligomeric protein, e.g., BMP2/BMP7, osteogenic protein, interleukin 1 converting enzyme (ICE), various interleukin receptors (e.g., the IL-18 receptor, IL-13 receptor, IL-4 receptor and IL-7 receptor), receptors of the nucleus such as retinoid receptors, T-cell receptors, integrins such as cell adhesion molecules, beta1-integrins, tumor necrosis factor receptor and soluble and membrane bound forms of class I and class II major histocompatibility complex proteins (MHC). For heteromeric complexes that are receptors, the invention encompasses both soluble and membrane bound forms of the polypeptides. Descriptions of additional heteromeric proteins that can be produced according to the invention can be found in, for example, *Human Cytokines: Handbook for Basic and Clinical Research, Vol. II* (Aggarwal and Gutterman, eds. Blackwell Sciences, Cambridge Mass., 1998); *Growth Factors: A Practical Approach* (McKay and Leigh, Eds. Oxford University Press Inc., New York, 1993) and *The Cytokine Handbook* (A W Thompson, ed.; Academic Press, San Diego Calif.; 1991).

As used herein, the term "fusion protein" refers to a protein, or domain of a protein (e.g., a soluble extracellular domain) fused to a heterologous protein or peptide. Examples of such fusion proteins include proteins expressed as a fusion with a portion of an immunoglobulin molecule, proteins expressed as fusion proteins with a zipper moiety, and novel polyfunctional proteins such as fusion proteins of cytokines and growth factors (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins. Any of the molecules herein described can be expressed as a fusion protein including but not limited to the extracellular domain of a cellular receptor molecule, an enzyme, a hormone, a cytokine, a portion of an immunoglobulin molecule, a zipper domain, and an epitope.

The invention finds particular utility in improving the production of heteromeric complexes via cell culture processes. The cell lines used in the invention can be genetically engineered to express a protein of commercial or scientific interest. By "genetically engineered" is meant that the cell line has been transfected, transformed or transduced with a recombinant polynucleotide molecule, so as to cause the cell to express a desired protein. Methods and vectors for genetically engineering cells and/or cell lines to express a protein of interest are well known to those of skill in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989).

In addition to the nucleic acid encoding the desired component of the heteromeric complex, vector constructs can include additional components to facilitate replication in prokaryotic and/or eukaryotic cells, integration of the construct into a eukaryotic chromosome, and markers to aid in selection of and/or screening for cells containing the construct. Vectors of the invention are recombinant DNA vectors including, but not limited to, plasmids, phages, phagemids, cosmids, viruses, retroviruses, and the like, which insert a desired nucleic acid into a cell.

A nucleic acid is "operably linked" when it is placed into a functional relationship with another nucleic acid. More specifically, operably linked means that two different nucleic acids encoding different polypeptides have transcription induced simultaneously. Operably linked is also intended to mean that the linked nucleic acids can be contiguous in a single transcriptional unit, while translation is directed from one or more ribosomal start sites (e.g., internal ribosomal start site).

The methods of the invention also can be used in combination with known or yet to be discovered methods of inducing the production of recombinant proteins. By "inducing conditions" is meant a technique to increase the relative production per cell of a desired recombinant protein. Such techniques include cold temperature shift, and additions of chemicals, and combinations of any known or yet to be discovered techniques, to name just a few examples, as well as any yet to be described and/or discovered induction techniques. Typically, a batch or a perfusion culture of cells at high density is induced to produce the recombinant protein. Often, other cell processes (such as growth and division) are inhibited so as to direct most of the cells' energy into recombinant protein production.

Any selectable marker having complementing subunits can be used in the methods and compositions of the invention. As used herein, the term "subunit" when referring to a selectable marker refers to a portion of a selectable marker. Further, a first subunit of a selectable marker can be expressed with a second different subunit of the same selectable marker to provide a level of selectable activity not present in either subunit alone. A subunit can also refer to a polypeptide having mutations that are complemented by another mutated polypeptide that is also a different subunit of the selectable marker.

Selectable markers that confer resistance to particular drugs that are ordinarily toxic to an animal cell can be used in the methods and compositions of the invention. For example, the following are non-limiting examples of resistance selectable markers: zeomycin (zeo); puromycin (PAC); Blasticidin S (BlaS), GPT, which confers resistance to mycophenolic acid (Mulligan & Berg (1981), Proc. Natl. Acad. Sci. USA 78:2072); the neomycin resistance gene, which confers resistance to the aminoglycoside G-418 (Colberre-Garapin et al. (1981), J. Mol. Biol. 150:1); and hygro, which confers resistance to hygromycin (Santerre et al. (1984), Gene 30:147).

Metabolic enzymes that confer cell survival or induce cell death under prescribed conditions can also be used in the methods and compositions of the inventions. Examples include but are not limited to: dihydrofolate reductase (DHFR); herpes simplex virus thymidine kinase (TK) (Wigler et al. (1977), Cell 11:223), hypoxanthine-guanine phosphoribosyltransferase (HGPRT) (Szybalska & Szybalski (1962), Proc. Natl. Acad. Sci. USA 48:2026), and adenine phosphoribosyltransferase (APRT) (Lowy et al. (1980), Cell 22:817), which are genes which can be employed in cells lacking TK, HGPRT or APRT, respectively.

In a particular embodiment, dihydrofolate reductase (DHFR) is the selectable marker used in the methods and compositions of the present invention. DHFR can also be used for antimetabolite resistance to methotrexate (Wigler et al. (1980), Natl. Acad. Sci. USA 77:3567; O'Hare et al. (1981), Proc. Natl. Acad. Sci. USA 78:1527). More particularly, as used in the invention, DHFR is divided into two subunits, F[1,2] and F[3] (from amino acids 1-105 and 106-187) and association of the subunits in a cell is promoted by interaction domains attached to the respective subunits (see Examples below; Pelletier et al. (1998), PNAS, 95:12141-12146). During the selection process, cells lack DHFR activity such that they will not grow in selection media (−GHT) without the DHFR activity. Growth is restored upon association of the DHFR fragments. Alternatively, cells expressing endogenous DHFR can be used and transfectants can be selected by conferring increased resistance to toxic levels of methotrexate.

Methotrexate can also be used in accordance with the invention to amplify recombinant nucleic acids after selection of −GHT sensitive cells. Selection is commonly at a concentration of 25 nM, more preferably 50 nM, even more preferably 150 nM and most preferably 300 nM of methotrexate. The skilled artisan will recognize that methotrexate concentrations can be as high as 500 nM or higher to amplify recombinant nucleic acids that give resistance to the drug, such as those described herein. Amplification using the vectors and methods of the invention is particularly advantageous because it has been found that in the case of expressing a heavy and light chain, both chains are amplified in roughly equal levels.

Selectable markers that are based on color selection can also be used in the methods and compositions of the invention. In a particular example, beta-galactosidase can be used (Blau et al., WO 98/44350). Fluorescence markers can also be used in the methods of the present invention, for example, GFP has been used for clonal selection of cells to measure protein interactions in protein-fragment complementation assays (Remy and Michnick (1999), Proc. Natl. Acad. Sci., 96:5394-5399). Similarly fluorescein-conjugated methotrexate can be used to detect cells expressing complementing DHFR fragments (Remy and Michnick (2001), Proc. Natl. Acad. Sci., 98:7678-83). An advantage for fluorescent markers is that this selection can be done in any animal cell type and is not restricted to those having a deficiency in a metabolic pathway, e.g., as with DHFR selection, or does not require a drug sensitivity, e.g., to neomycin.

As used herein, the term "polypeptide" includes naturally occurring or recombinantly expressed proteins, including pre- and post-translational processing, or fragments thereof, which typically retain secondary structure. Proteins are large molecules with high molecular weights (from about 10,000 for small ones [of 50-100 amino acids] to more than 1,000,000 for certain forms); they are composed of varying amounts of the same 20 amino acids, which in the intact protein are united through covalent chemical linkages called peptide bonds. The amino acids, linked together, form linear unbranched polymeric structures called polypeptide chains; such chains can contain hundreds of amino acid residues; these are arranged in specific order for a given species of protein. The term "peptide" includes short fragments of polypeptides or proteins, of typically less than 20 amino acids in length.

The term "cell culture" is meant to include the growth and propagation of cells outside of a multicellular organism or tissue. Typically, cell culture is performed under sterile, controlled temperature and atmospheric conditions in tissue culture plates (e.g., 10-cm plates, 96 well plates, etc.), or other adherent culture (e.g., on microcarrier beads) or in suspension culture such as in roller bottles. Cultures can be grown in shake flasks, small scale bioreactors, and/or large-scale bioreactors. A bioreactor is a device used to culture cells in which environmental conditions such as temperature, atmosphere, agitation, and/or pH can be monitored and adjusted. A number of companies (e.g., ABS Inc., Wilmington, Del.; Cell Trends, Inc., Middletown, Md.) as well as university and/or government-sponsored organizations (e.g., The Cell Culture Center, Minneapolis, Minn.) offer cell culture services on a contract basis.

Optimal periods for which the cultures are in contact with agents that select for the selectable activity are for longer than the typical period for one normal growth cycle (e.g., for Chinese hamster ovary cells (CHO cells), where one growth cycle has been reported to be approximately 20-22 hours (Rasmussen et al. (1998), Cytotechnology, 28:31-42)). As such, in one embodiment, the cultures comprise selectable conditions, e.g., drugs, metabolites, or color substrates, preferably for at least about one day, more preferably for at least about 3 days, and even more preferably for at least about 7 days.

A wide variety of animal cell lines suitable for growth in culture are available from, for example, the American Type Culture Collection (ATCC, Manassas, Va.) and NRRL (Peoria, Ill.). Some of the more established cell lines typically used in the industrial or academic laboratory include CHO, VERO, BHK, HeLa, Cos, CV1, MDCK, 293, 3T3, PC12, mycloma (e.g., NSO), and WI38 cell lines, to name but a few examples. In other embodiments, non-animal cell lines can be used in the methods of the invention, for example, plant cell lines, insect cell lines (e.g., sf9), yeast cells or bacterial cells such as E. coli.

In particular embodiments, the dihydrofolate reductase (DHFR)-deficient mutant cell line (Urlaub et al. (1980), Proc Natl Acad Sci USA 77:4216-4220), DXB11 and DG-44, are the CHO host cell lines of choice because the efficient DHFR selectable and amplifiable gene expression system allows high level recombinant protein expression in these cells (Kaufman R. J. (1990), Meth Enzymol 185:527-566). In addition, these cells are easy to manipulate as adherent or suspension cultures and exhibit relatively good genetic stability. In addition, new animal cell lines can be established using methods well known by those skilled in the art (e.g., by transformation, viral infection, and/or selection).

As noted above, a variety of host-expression vector systems can be utilized to express the heteromeric complexes of the invention. Where the heteromeric complex is soluble, the peptide or polypeptide can be recovered from the culture, i.e., from the host cell in cases where the heteromeric complexes are not secreted, and from the culture media in cases where the heteromeric complexes are secreted by the cells. However, the expression systems also encompass engineered host cells that express the heteromeric complexes anchored in the cell membrane.

Purification or enrichment of the heteromeric complexes from such expression systems can be accomplished using appropriate detergents and lipid micelles and methods well known to those skilled in the art. However, such engineered host cells themselves can be used in situations where it is important not only to retain the structural and functional characteristics of the heteromeric complexes, but also to assess biological activity, e.g., in drug screening assays.

The protein expressed by the methods of the invention can be collected. In addition the protein can be purified, or partially purified, from such culture or component (e.g., from culture medium or cell extracts or bodily fluid) using known processes. The phrase "partially purified" means that some fractionation procedure, or procedures, have been carried out, but that more polypeptide species (at least 10%) than the desired protein is present. By "purified" is meant that the protein is essentially homogeneous, i.e., less than 1% contaminating proteins are present. Fractionation procedures can include but are not limited to one or more steps of filtration, centrifugation, precipitation, phase separation, affinity purification, gel filtration, ion exchange chromatography, size exclusion chromatography (SEC), hydrophobic interaction chromatography (HIC; using such resins as phenyl ether, butyl ether, or propyl ether), HPLC, or some combination of above.

The invention also optionally encompasses further formulating the proteins. By the term "formulating" is meant that the proteins can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration.

The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

The invention having been described, the following examples are offered by way of illustration and not limitation.

EXAMPLES

Example 1

Construction of DHFR Complementation Vectors

Construction of recombinant vectors expressing subunits of a selectable marker was performed as follows. Dihydrofolate reductase (DHFR) was chosen as the selectable marker to be used in the following experiments. Previous work has shown that due to its modular three-dimensional structure, DHFR can be broken into two parts and when expressed as a fusion protein having an interaction domain, the subunits can then be reassociated in a cell providing selectable activity. See FIG. 1 for a general overview of the order of the various nucleic acids described in one embodiment of the invention.

Sequential polymerase chain reaction (PCR) SOEing was utilized to generate nucleic acids suitable for cloning into expression vectors that encode a fusion of a leucine zipper interaction domain fused to a linker polypeptide fused to a subunit of DHFR. Briefly, PCR SOEing is splicing of genes by overlap extension for recombining DNA molecules at junctions without the use of restriction endonucleases or ligase (Methods in Molecular Biology, Vol. 15, "PCR protocols: Current Methods and Applications," and "Chapter 25: In Vitro Recombination," Editor. B. A. White, 1993, Humana Press, Inc., Totowa, N.J.; and Mutagenesis of DNA, Robert M. Horton, pp.251-261).

Fragments from the genes that are to be recombined are generated in separate polymerase chain reactions (PCRs). The primers are designed so that the ends of the products contain complementary sequences, such as a common restriction site, i.e., BamH1. When these PCR products are subsequently mixed, denatured, and reannealed, the strands having the matching sequences at their 3' ends overlap and act as primers for each other (Horton et al. (1989), Gene, 77(1):61-8).

The primers used in the present example are as follows:

```
JM238    5'-ATATCTCGAGATCCGTGCCATCATGTCTGACCGTATGAA
                                                AC-3'
JM239    5'-GCCACCGCCGGATCCACCGCCACCCCGCTCGCCTACCAG
                                             CTTTT-3'
JM240    5'-GGTGGATCCGGCGGTGGCGGCGGCTCAATGGTTCGACCA
                                            TTGAAC-3'
PDHFR106 5'-ATATCAATTGTTATTCCGGTTGTTCAATAAGTC-3'
JM242    5'-GTGGATCCGGCGGTGGCGGCGGCTCATTGGCAAGTAAAG
                                            TAGACA-3'
JM244    5'-ATATCAATTGTTAGTCTTTCTTCTCGTAGACTT-3'
```

The following strategy was employed to create a nucleic acid encoding a leucine zipper interaction domain fused in frame to a linker fused in frame to DHFR amino acids 1-105. The first PCR reaction amplified the yeast GCN4 leucine zipper (Lz) using primers JM238 (SEQ ID NO:1) and JM239 (SEQ ID NO:2). All PCR reactions utilized Roche Expand High Fidelity PCR system, which included all of the required reagents, except for 10 mM dNTP's, which are commercially available. Thermal cycle conditions (PCR condition 1) were as follows:
94° C. for 5 min
94° C. for 30 sec ⎯⎯⎯⎯
37° C. for 30 sec |⎯⎯ 25 cycles
72° C. for 30 sec ⎯⎯⎯⎯
72° C. for 7 minutes
4° C. (hold).

The JM238 primer has a Xho1 site at the 5' terminus and the JM239 primer has a BamH1 site at the 5' terminus. At the same time, primers JM240 (SEQ ID NO:3) and PDHFR106 (SEQ ID NO:4) were used to PCR amplify the DHFR subunit encoding amino acids 1-105 of DHFR (SEQ ID NO:5) [same as above, except with a 1 minute duration at 94° C. and at 72° C. for the 25 cycles (PCR condition 2)]. JM240 has a BamH1 site at its 5' terminus and PDHFR106 has a Mfe1 site at its 5' terminus. Each respective PCR product was gel purified using standard gel purification techniques, and a second PCR reaction was performed using PCR condition 2. The resulting product was then cloned into a pGEM-T vector (Promega) and sequenced.

A similar strategy was employed to create a nucleic acid encoding a leucine zipper fused in frame to a linker fused in frame to DHFR amino acids 106-187. The first PCR reaction amplified the yeast GCN4 leucine zipper using primers JM238 (SEQ ID NO:1) and JM239 (SEQ ID NO:2) using PCR condition 1. The JM238 primer has a Xho1 site at the 5' terminus and the JN239 primer has a BamH1 site at the 5' terminus. At the same time, primers JM242 (SEQ ID NO:6) and JM244 (SEQ ID NO:7) were used to PCR amplify the DHFR subunit encoding amino acids 106-187 of DHFR (SEQ ID NO:5) using PCR Condition 1. JM242 has a BamH1 site at its 5' terminus and JM244 has a Mfe1 site at its 5' terminus. Each respective PCR product was gel purified using standard gel purification conditions, and a second PCR reaction was performed using PCR Condition 1. The resulting product was then cloned into a pGEM-T vector (Promega) and sequenced.

Once the correct sequences were verified, the Lz-linker-DHFR 1-105 (363 bp) and Lz-linker-DHFR 106-187 (343 bp) fragments were cut from the pGEM-T vector with Xho1 and Mfe1 and the nucleic acids were gel purified. The vector pDC317 was digested with Not1 and Xho1 and the 558 bp internal ribosomal entry site (IRES) element was recovered by gel purification. Since Xho1 is not a unique site on pDC317, a triple ligation between the Not1/Xho1 IRES element, the Xho1/Mfe1 Lz-linker-DHFR 1-105 and Lz-linker-DHFR 106-187 was performed in pDC317 and isolates were tested and confirmed to have successful ligation by restriction digest.

The antibody (Ab) heavy and light chain genes, encoding an antibody which specifically recognizes the murine interleukin 4-receptor (IL4R), were each cloned into the vectors prepared as described above. Anti-IL4R heavy chain (HC) was digested with Not1 and Sal1. From this digestion, a 1413 bp fragment was isolated by gel purification. Likewise, light chain (LC) of the anti-IL4R antibody, was cut from a vector with the same enzymes and the 736 bp light chain fragment was gel purified. The Lz-LINKER-DHFR-pDC317 vectors (both 1-105 and 106-187) were also cut with Not1 and Sal1 and the heavy and light chains were cloned into the corresponding expression vectors. The following combinations were obtained:
IL4R Ab HC: Lz-linker-DHFR 1-105 pDC317
IL4R Ab LC: Lz-linker-DHFR 106-187 pDC317

IL4R Ab LC: Lz-linker-DHFR 1-105 pDC317
IL4R Ab HC: Lz-linker-DHFR 106-187 pDC317

Example 2

Construction of a Second Set of DHFR Complementation Vectors

Construction of a second set of recombinant vectors expressing subunits of a selectable marker was performed as follows. Bicistronic vectors containing the internal ribosomal entry site (IRES) are based on pED4 (Kaufman (1991), Nuc Acids Res. 19(16):4485-4490). The base vector, pDC318, is a derivative of pG2.1 (Aldrich (1998), Cytotechnology, 28:9-17) containing a truncated 600 base pair portion of the expression augmenting sequence element (EASE). pDC317 is a similar vector which contains the larger 3.6 kilobase EASE. PCR was used to fuse a GCN4 leucine zipper (LZ) and flexible linker to two separate fragments of the selectable marker dihydrofolate reductase (DHFR). The first fragment extends from amino acids 1-105 and the second fragment includes amino acids 106-187. The final PCR products were then cloned into pDC317 or pDC318 just downstream of the IRES element.

The IRES element was modified based on the pED3 vector created by Davies et al., to enhance translation of the LZ-linker-DHFR fragments (Davies (1992), J. Virol., 66(4): 1924-1932). This change was incorporated into the IRES LZ-linker-DHFR fragments in pDC317 via PCR using the primer JM256 (5'-GATAATATGGCCACAACCATGTCT-GACCGTATGAAACA-3') (SEQ ID NO:8. The underlined ATG marks the transition from the pED3 IRES to the LZ. The fragments were subsequently subcloned into pGEM-T (Invitrogen) containing the full length IRES sequence. The pED3 IRES LZ-linker-DHFR 1-105 and 106-187 fragments were then cloned into pDC318 in order to create pDC321 and pDC322 or pDC317 to create pDC323 or pDC324, respectively.

The murine anti-IL4R antibody chains were cloned into the multiple cloning sites of pDC321 and pDC322, just upstream of the pED3 IRES to create pDC321 LC, pDC321 HC, pDC322 LC, and pDC322 HC. Similarly, the heavy and light chains were cloned into the multiple cloning sites of pDC323 and pDC324 to create pDC323 LC, pDC323 HC, pDC324 LC, and pDC324 HC.

Example 3

Transfection and Selection

Transfection of the above vectors was performed into DHFR deficient CHO cell line. Standard transfection protocols were used. Cells were incubated at 37° C. until in log phase, and transfected with an appropriate concentration of purified plasmids with 150 uL Lipofectamine (Gibco BRL) as recommended by the manufacturer. The Lipofectamine (Invitrogen) transfections were performed with a 6:6:1 ratio of either pDC321 LC:pDC322 HC:pCDNA3 (Invitrogen), pDC321 HC:pDC322 LC:pCDNA3, pDC323 LC:pDC323 HC:pCDNA3, or pDC324 HC:pDC324 LC:pCDNA3.

Initial selection was performed in shake flasks in non-DHFR selection media plus G418 with recovery of up to 70% viability, followed by selection in DHFR selection media lacking glycine, hypoxanthine and thymidine (-GHT) with recovery of up to 90% viability. Pools established following G418 and -GHT selection were exposed to 25 nM methotrexate in an attempt to amplify the antibody chains and thereby enhance antibody production in the pools. Both the unamplified and amplified pools demonstrate stable production of antibody during this time period.

For cloning, transfected cells were diluted and plated directly in 96 well plates in -T growth media. No pre-selection in G418 or -GHT media was needed.

For the pDC321 and pDC322 vectors, the unamplified pool maintained a qP of 1 µg/$10^6$ cells/day. An increase in the qP for the amplified pool correlates to an increase in viability after recovery of the cells from selection. The qP of the amplified pool ranged from 8-18 µg/$10^6$ cells/day, indicating an 8-18 fold increase in antibody production compared to the unamplified pool. Five independent pools have been evaluated and found to exhibit similar expression levels. In addition to analysis of the pools, two of the clones were scaled up to shake flasks, amplified with 25 nM methotrexate, and evaluated for expression. Expression was similar to the results described for the pools.

For the pDC323 and pDC324 vectors, namely the vectors with the 3.6 kilobase EASE element, the unamplified pool maintained a qP of about 5 µg/$10^6$ cells/day.

Example 4

Expression of Antibodies from the Complementation Vectors

Unamplified and amplified pools were then evaluated under simulated production conditions. A shift to lower temperature, e.g., 31° C. leads to higher titers. Induction was performed in 20 mL shake flask cultures shifted to the lower temperature. Antibody titers were measured by ELISA. An unamplified pool produced 80 µg/mL of antibody in 9 days, while maintaining a final viability of 65.8%. Three independent pools were analyzed. The amplified pools produced an average of 407.8 µg/mL of antibody in 10 days, with an average final viability of 47.2%. The specific productivity's (qP) of the pools ranged from 10-20 µg/$10^6$ cells/day.

Example 5

Western Blot Analyses of Antibodies

Antibodies expressed from the cells transfected with the pDC321 or pDC322 vectors were isolated using standard methods, purified and run on denaturing as well as native gels. A 4-20% Tris Glycine gel of 1 mm, 10 well was run (Invitrogen, Cat. No. E6025) at 125 V for about 2 hours. The samples were not heated and were suspended in 2×Native Gel Tris Glycine Sample buffer (Invitrogen, Cat. No. LC2673) with (reduced) or without (non-reduced) 5% beta mercaptoethanol (2.5% final concentration). The sample buffer was 1×SDS running buffer. The gels were non-denaturing as there was no SDS or reducing agents in the gel itself, only the sample buffers as indicated.

Transfer to nitrocellulose (Nitrocellulose Membrane Filter Paper Sandwich, Invitrogen, LC2001) was performed for 45 minutes at 33 V. The membranes were blocked overnight at 4 C in 5% nonfat dry milk in PBST (0.1% Tween 20) or "blotto" solution. The blotting grade affinity purified goat anti-mouse IgG (H+L) HRP conjugate antibody (Bio-Rad, Cat No.170-6516) was diluted 1:2000 in blotto solution and applied to the blots for 2.5 hours. The blots were then rinsed 5×for 5 minutes each in PBST and developed for 30 seconds with the ECL western blotting detection reagents (Amersham Pharmacia Biotech, Cat. No. RPN2106).

The samples were all derived from supernatants from passage 90 of the cultures. Specifically, the purified antibody was taken from an induced, unamplified culture and purified on a protein G column. The 0 nM supernatant was concentrated to 10× on a Millipore concentrator (UFV2BCC40) at 3000 rpm, since its concentration by Mu FC ELISA was lower than the other samples. The non-reduced gel showed that the antibody with heavy and light chain is present in all cases and that there is very little free light chain or dimerized light chain in the 25 and 50 nM supernatants, while none was apparent in the 0 nM supernatants and there is some dimerized light chain in the purified Ab.

The heavy chains and light chains were present in all of the supernatants in equal proportions as the purified antibody, and significantly, there is considerably more total antibody in the methotrexate amplified supernatants, consistent with the results of Example 3.

Antibodies were also purified from cells transfected with the pDC323 or pDC324 vectors. The antibodies from the supernatants of the cells had equal proportions of heavy and light chains on the non-reduced gel, with very little free light chain or dimerized light chain.

Example 6

FACS Analysis of DHFR Expression

Fluorescence activated cell sorting (FACS) analysis was employed in order to verify a concurrent amplification of DHFR expression following methotrexate exposure. Unamplified and amplified pools were labeled with fluorescein labeled methotrexate, which binds DHFR, and analyzed on a FACS Calibur analyzer. Unlabeled, untransfected CS9 cells were used as a control. Both unamplified and amplified pools show DHFR activity, as expected. A larger degree of fluorescence is observed in the 25 nM methotrexate amplified pool as compared to the 0 nM methotrexate unamplified pool. This verifies that amplification of antibody expression correlates with an amplification of DHFR expression.

EQUIVALENTS AND REFERENCES

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A vector comprising a first nucleic acid encoding a first immunoglobulin heavy chain or immunoglobulin light chain, wherein the transcription of said first nucleic acid is operably linked to transcription of a second nucleic acid encoding a first subunit of a selectable marker, and further comprising a third nucleic acid encoding a second immunoglobulin light chain or immunoglobulin heavy cahin wherein the immunoglobulin light chain is capable of associating with the first immunoglobulin heavy chain to form a heteromeric complex, wherein the transcription of said third nucleic acid is operably linked to transcription of a fourth nucleic acid which encodes a second subunit of a selectable marker, and wherein said second subunit associates with the first subunit of the selectable marker, to provide a selectable activity, and the vector is capable of being transfected into mammalian cells and improving selection of said cells.

2. The vector of claim 1 wherein the first nucleic acid encodes immunoglobulin light chain, and the third nucleic acid encodes an immunoglobulin heavy chain.

3. The vector of claim 2, wherein the selectable marker is selected from the group consisting of a drug resistance marker, a metabolic survival marker, a color marker and a fluorescent marker.

4. The vector of claim 3, wherein the selectable marker is selected from the group consisting of dihydrofolate reductase, neomycin resistance, hygromycin resistance, beta-galactosidase, and green fluorescent protein.

5. The vector of claim 1, wherein an internal ribosomal entry site occurs between the first nucleic acid and the second nucleic acid.

6. The vector of claim 2, wherein an internal ribosomal entry site occurs between the third nucleic acid and the fourth nucleic acid.

7. The vector of claim 2, wherein each of the first and second selectable marker subunit is fused to an interaction domain.

8. The vector of claim 7, wherein the interaction domain is a dimerization sequence that is a leucine zipper from a polypeptide selected from the group consisting of GCN4, C/EBP, c-Fos, c-Jun, c-Myc and c-Max.

9. The vector of claim 2, further encoding a different functional selectable marker selected from the list consisting of zeomycin, neomycin, puromycin, Blasticidin S, and GPT.

10. An isolated host cell that has been genetically engineered to contain the vector of claim 2.

11. The host cell of claim 10, which is selected from the group consisting of CHO, VERO, BHK, HeLa, Cos, MDCK, 293, 3T3, a myeloma cell line, and WI38 cells.

12. A method of producing an antibody heavy chain and light chain heterocomplex comprising the step of culturing the host cell of claim 11 under conditions wherein the heteromeric complex is expressed by the host cell.

13. The method of claim 12, wherein the heteromeric complex is an antibody.

14. The method of claim 12, further comprising isolating the heteromeric complex.

15. An expression system comprising a first vector encoding a bicistronic transcript comprising a first nucleic acid encoding a first immunoglobulin heavy chain or immunoglobulin light chain, wherein transcription of said first nucleic acid is operably linked to transcription of a second nucleic acid encoding a first subunit of a selectable marker, and a second vector encoding a bicistronic transcript comprising a third nucleic acid encoding a second immunoglobulin light chain or immunoglobulin heavy chain wherein the immunoglobulin light chain is capable of associating with the first immunoglobulin heavy chain to form a heteromeric complex, wherein transcription of said third nucleic acid is operably linked to transcription of a fourth nucleic acid encoding a second subunit of a selectable marker, and wherein said first and second selectable marker subunits associate to provide a selectable activity, wherein the expression system is capable of being transfected into mammalian cells and improving selection of said cells.

16. The expression system of claim 15 wherein the first nucleic acid encodes immunoglobulin light chain, and the third nucleic acid encodes an immunoglobulin heavy chain.

17. The expression system of claim 15, wherein the selectable marker is selected from the group consisting of a drug resistance marker, a metabolic survival marker, a color marker and a fluorescent marker.

18. The expression system of claim 17, wherein the selectable marker is selected from the group consisting of dihydrofolate reductase, neomycin resistance, hygromycin resistance, betagalactosidase, and green fluorescent protein.

19. The expression system of claim 15, wherein an internal ribosomal entry site occurs between the first nucleic acid and the second nucleic acid.

20. The expression system of claim 15, wherein an internal ribosomal entry site occurs between the third nucleic acid and the fourth nucleic acid.

21. The vector composition of claim 15, wherein each of the first and second selectable marker subunit is fused to an interaction domain.

22. The expression system of claim 21, wherein the interaction domain is a leucine zipper from a polypeptide selected from the group consisting of GCN4, CIEBP, c-Fos, c-Jun, c-Myc and c-Max.

23. The expression system of claim 15, wherein the second nucleic acid and the fourth nucleic acid further encode a different functional selectable marker selected from the list consisting of zeomycin, neomycin, puromycin, Blasticidin S, and GPT.

24. An isolated host cell genetically engineered to contain the expression system of claim 15.

25. The host cell of claim 24, which is selected from the group consisting of CHO, VERO, BHK, HeLa, Cos, MDCK, 293, 3T3, a myeloma cell line, and WI38 cells.

26. A method of producing an antibody heavy chain and light chain heterocomplex comprising the step of culturing the host cell of claim 25 under conditions wherein the heteromeric complex is expressed by the host cell.

27. The method of claim 26, further comprising isolating the heteromeric complex.

28. An expression system comprising a first vector comprising a first nucleic acid encoding a light chain of an antibody wherein the transcription of said light chain is operably linked to the transcription of a second nucleic acid that encodes a fusion polypeptide of a first subunit of dihydrofolate reductase fused to a dimerization sequence, and a second vector comprising a third nucleic acid encoding a heavy chain of an antibody wherein the transcription of said heavy chain is operably linked to the transcription of a fourth nucleic acid that encodes a fusion polypeptide of a second subunit of a dihydrofolate reductase fused to a dimerization sequence wherein each subunit of dihydrofolate reductase does not have selectable activity when expressed alone and co-expression of the first dihydrofolate reductase subunit with the second dihydrofolate reductase subunit provides dihydrofolate reductase activity, wherein the expression system is capable of being transfected into mammalian cells and improving selection of said cells.

29. The expression system of claim 28, wherein one subunit of dihydrofolate reductase is amino acids 1 to 105 of SEQ ID NO:5 and the other subunit of dihydrofolate reductase is amino acids 106 to 187 of SEQ ID NQ:5.

30. The expression system of claim 28, wherein the dimerization sequence fused to the dihydrofolate reductase subunit is derived from the GCN4 leucine zipper sequence.

31. An isolated host cell transfected with the expression system of any of claims 28, 29, or 30.

32. An expression system comprising a first vector encoding a bicistronic transcript comprising a first nucleic acid encoding a desired polypeptide, wherein transcription of said first nucleic acid is operably linked to transcription of a second nucleic acid encoding a first subunit of a selectable marker, and a second vector encoding a bicistronic transcript comprising a third nucleic acid, wherein transcription of the third nucleic acid is operably linked to transcription of a fourth nucleic acid encoding a second subunit of a selectable marker, and wherein said first and second selectable marker subunits associate to provide a selectable activity, and the expression system is capable of being transfected into mammalian cells and improving selection of said cells, and the first nucleic acid encodes an antibody heavy chain and the third nucleic acid encodes an antibody light chain.

33. The expression system of claim 32, wherein the selectable marker is selected from the group consisting of dihydrofolate reductase, neomycin resistance, hygromycin resistance, betagalactosidase, and green fluorescent protein.

34. The expression system of claim 33, wherein each of the first and second selectable marker subunit is fused to an interaction domain.

35. The expression system of claim 34, wherein the interaction domain is a leucine zipper from a polypeptide selected from the group consisting of GCN4, C/EBP, c-Fos, c-Jun, c-Myc and c-Max.

36. An isolated host cell genetically engineered to contain the expression system of claim 35.

* * * * *